US006800671B1

(12) United States Patent
Montgomery et al.

(10) Patent No.: US 6,800,671 B1
(45) Date of Patent: Oct. 5, 2004

(54) LOW PEAK EXOTHERM CURABLE COMPOSITIONS

(75) Inventors: Robert Eric Montgomery, Monterey, MA (US); Anthony J. Cipolla, Trout Run, PA (US)

(73) Assignee: BriteSmile, Inc., Walnut Creek, CA (US)

( * ) Notice: Subject to any disclaimer, the term of this patent is extended or adjusted under 35 U.S.C. 154(b) by 0 days.

(21) Appl. No.: 09/552,994

(22) Filed: Apr. 21, 2000

(51) Int. Cl.$^7$ .................. C08J 101/00; C08J 105/00
(52) U.S. Cl. ............... 523/105; 525/54.3; 525/242; 525/244; 525/259; 525/301; 525/313
(58) Field of Search .................. 523/105; 525/242, 525/244, 259, 301, 313, 191, 54.3

(56) References Cited

U.S. PATENT DOCUMENTS

| | | |
|---|---|---|
| 4,689,015 A | 8/1987 | Denyer et al. |
| 4,771,089 A | 9/1988 | Ofstead |
| 4,859,716 A | 8/1989 | Ibsen et al. |
| 4,938,763 A | 7/1990 | Dunn et al. |
| 5,006,571 A * | 4/1991 | Kumar et al. ............... 523/120 |
| 5,100,992 A | 3/1992 | Cohn et al. |
| 5,204,383 A | 4/1993 | Manabe et al. |
| 5,240,989 A | 8/1993 | Bernard et al. |
| 5,278,201 A | 1/1994 | Dunn et al. |
| 5,410,016 A | 4/1995 | Hubbell et al. |
| 5,472,991 A | 12/1995 | Schmitt et al. |
| 5,525,647 A | 6/1996 | Eichmiller |
| 5,530,038 A | 6/1996 | Yamamoto et al. |
| 5,534,562 A | 7/1996 | Jensen et al. |
| 5,541,000 A | 7/1996 | Hardy et al. |
| 5,587,406 A | 12/1996 | Yamamoto et al. |
| 5,708,052 A | 1/1998 | Fischer et al. |
| 5,844,016 A | 12/1998 | Sawhney et al. |
| 5,849,266 A | 12/1998 | Friedman |
| 5,876,744 A * | 3/1999 | Della Valle et al. ........ 424/434 |
| 5,900,245 A | 5/1999 | Sawhney et al. |
| 5,936,035 A | 8/1999 | Rhee et al. |
| 6,030,634 A | 2/2000 | Wu et al. |
| 6,037,385 A | 3/2000 | Smith |
| 6,048,202 A | 4/2000 | Jensen et al. |
| 6,086,370 A | 7/2000 | Jensen et al. |
| 6,153,216 A * | 11/2000 | Cordes et al. ............... 424/449 |
| 6,187,836 B1 * | 2/2001 | Oxman et al. ............... 522/148 |
| 6,291,593 B1 * | 9/2001 | Cheng ........................ 525/292 |

FOREIGN PATENT DOCUMENTS

| | | |
|---|---|---|
| WO | 9317669 | 9/1993 |
| WO | 9836700 | 8/1998 |

OTHER PUBLICATIONS

Nikitin, The Chemistry of Cellulose and Wood, p. 62–71 (1966).*
Mandelkern, An Introduction to Macromolecules, p. 19–27, Springer Verlag (1983).*
Hiemenz, Polymer Chemistry, p. 34–43, Marcel Dekker (1984).*
Fried, Polymer Science and Technology, "1.3 Molecular Weight", p. 16–18, Prentice Hall (1995).*
Spadaro et al., "Silver Polymethyl Methacrylate Antibacterial Bone Cement," *Clinical Orthopaedics and Related Research*, 143: 266–270 (1979).
Mathias et al., "Allergic Contact Dermatitis From Anaerobic Acrylic Sealants," *Arch. Dermatol.*, 120: 1202–1205 (1984).
Gurny et al., "Bioadhesive Intraroral Release Systems: Design, Testing and Analysis," *Biomaterials*, 5: 336–340 (1984).
Baker et al., "The Release of Residual Monomeric Methyl Methacrylate from Acrylic Appliances in the Human Mouth: An Assay for Monomer in Saliva," *J. Dent. Res.*, 67: 1295–1299 (1988).
Tobler et al., "Contact Dermatitis from Acrylate and Methacrylate Compounds in Lowicryl® Embedding Media for Electron Microscopy," 23: 96–102 (1990).
Kanerva, et al., "Occupational Allergic Contact Dermatitis Caused by Exposure to Acrylates During Work With Dental Prostheses," *Contact Dermatitis*, 28: 268–275 (1993).
Guo, Jian–Hwa, "Investigating the Surface Properties and Bioadhesion of Buccal Patches," *J. Pharm. Pharmacol.*, 46: 647–650 (1994).
Kanerva, et al., "Occupational Allergic Contact Dermatitis from 2–hydroexthyl Methacrylate and Ethylene Glycol Dimethacrylate in a Modified Acrylic Structural Adhesive," *Contact Dermatitis*, 33: 84–89 (1995).
Guo et al., "The Effects of Backing Materials and Multilayered Systems on the Characteristics of Bioadesive Buccal Patches," *J. Pharm. Pharmacol.*, 48: 255–257 (1996).
Hume et al., "Bioavailability of Components fo Resin–Based Materials Which Are Applied to Teeth," *Crit. Rev. Oral Biol. Med.*, 7: 172–179 (1996).
Peppas et al., "Hydrogels as Mucoadhesive and Bioadhesive Materials: A Review," *Biomaterials*, 17: 1553–1561 (1996).
DeGrande et al., "Specialized Oral Mucosal Drug Delivery Systems: Patches," pp. 285–315 in *Oral Mucosal Drug Delivery*, ed. Michael J. Rathbone (1996).
Hemmer et al., "Allergic Contact Dermatitis to Artificial Fingernails Prepared From UV Light–Cured Acrylates," *Journal of the American Academy of Dermatology*, 35: 377–380 (1996).
Lönnroth et al., "Use of Polymer Materials in Dental Clinics, Case Study," *Swed. Dent.J.*, 21: 149–159 (1997).
Kanerva et al., "10 Years of Patch Testing With the (Meth) acrylate Series," *Contact Dermatitis*, 37: 255–258 (1997).
Chung et al., "Sensitization Potentials of Methyl, Ethyl, And n–Butyl Methacrylates And Mutual Cross–Sensitivity in Guinea Pigs," *The Journal of Investigative Dermatology*, 68: 187–190 (1977).
Lipman, Roger, "Hydrocolloid PSAs: New Formulation Strategies," *Medical Devices & Diagnostic Industry*, 132–148 (1999).

* cited by examiner

Primary Examiner—Jeffrey Mullis
(74) Attorney, Agent, or Firm—Mayer, Brown, Rowe & Maw LLP

(57) ABSTRACT

Compositions having a curable unsaturated compound, an adhesion promoter and curing agent which have a peak exotherm of less than 50° C. are disclosed. The compositions when cured are flexible bioadhesives which are also disclosed. Non-curable diluents can be included in the compositions. Flexible bioadhesives formed on biological structures and having low peak exotherms upon curing of curable compositions to form the flexible bioadhesives are disclosed. Compositions having a curable unsaturated compound and a curing agent and a peak exotherm of less than 50° C. are included in the invention.

37 Claims, No Drawings

LOW PEAK EXOTHERM CURABLE COMPOSITIONS

The present invention relates to low peak exotherm curable compositions that upon curing are useful as bioadhesives. The compositions of the invention can be placed in contact with one or more skin or mucosal surfaces, or other tissue surfaces, in an initially liquid or malleable form, then subsequently cured or polymerized in place to a final flexible solid or rubbery form.

BACKGROUND OF THE INVENTION

A broad spectrum of bioadhesives and bioadhesive compositions have been developed, for example, to adhere transdermal patches to the skin and to affix transmucosal patches to mucosal surfaces. In general, the purpose of such bioadhesives is to maintain intimate and prolonged contact with the underlying living tissue surface, in order to allow for the migration of medicinals into the body. In addition, bioadhesive compositions include those that merely adhere a physical barrier, such as a bandage, to living tissue (primarily for the purpose of protecting an underlying wound or compromised tissue surface from potential environmental insults, such as microorganisms). The majority of such bioadhesives are provided as films of varying thicknesses that, upon contact with a biological substrate such as skin or mucosa, display adhesive characteristics suitable for the intended use. For example, a transdermal patch comprises several layers, which may include a protective backing, a drug reservoir and/or matrix, an adhesive layer, and a release film layer. Each layer serves a unique purpose in the delivery of the active drug from the patch to the patient. The adhesive layer provides for the intimate and prolonged contact of the patch with the underlying skin, in order that the active drug may efficiently migrate from the patch reservoir and/or matrix into the skin.

Transmucosal patches are similar in construction, but differ in their adhesion specificity. Since mucosal surfaces (lining of the oral cavity, nasal passages, etc) are relatively moist, effective adhesives generally contain high molecular weight, water-soluble or -swellable polymers that become entangled with tissue surface polymers (such as mucins) upon contact with the moist mucosal surface. Varying the composition of the adhesive layer of the patch can control the strength and duration of contact with the mucosal surface. Transmucosal patches (also known as buccal patches when placed in the oral cavity) can be unidirectional (that is, it releases a drug only in the direction of the mucosal surface to which it is attached) or bidirectional (releases a drug, or other active substance, both in the direction of the mucosal surface, as well as into the rest of the oral cavity). A more thorough review of the subject of bioadhesion to mucosal surfaces can be found in Peppas, N. A. and Sahlin, J. J., *Hydrogels as Mucoadhesive and Bioadhesive Materials: A Review*, Biomaterials 17 (1996), 1553–1561, which is herein incorporated by reference.

Transdermal and transmucosal patches must also display physical characteristics appropriate to their intended use. Since the underlying biological substrate to which the patches become attached is flexible, patient comfort must be provided for by also formulating and constructing the patches from flexible components. Patch flexibility also allows for movement of the tissue underlying the patch without detachment or separation of the adhesive layer and subsequent loss of the patch.

One drawback of existing transdermal and transmucosal patches is their limited ability to conform to biological substrates that are not relatively flat. For instance, many transdermal patches are adhered to the upper arm, which is a relatively flat surface that provides an easy attachment point for a flat, flexible film patch. However, attachment of such a patch to a more contoured surface, such as on the knuckles of the hand, would be problematical without the ability of the patch to flex and conform in multiple dimensions, especially during movement of the underlying skin.

Transmucosal patches suffer from the same limitations of underlying tissue surface topography, made more difficult by the complexity and difficulty of adhering to a moist substrate, such as the oral mucosa lining the inside of the mouth. For this reason, transmucosal patches are generally small in order to allow them to be placed in a location that may be relatively flat, thus increasing the likelihood of successful, long-term adhesion.

Oral mucosal barrier compositions that are placed in contact with gingival tissue and cured in place to provide a physical barrier against contact of the underlying soft tissue with dental compositions such as tooth bleaching agents and acid etching compositions have been disclosed. Photopolymerizable dental resins have been used for this purpose in the past, generally comprising a curable monomer or blend of monomers (such as bis-GMA and triethyleneglycol dimethacrylate), together with a curing system (such as camphorquinone and dimethylaminomethyl methacrylate). Compositions such as these are described in U.S. Pat. No. 6,048,202 and in WO 98/36700 and are believed to be commercially available from Ultradent Products, Inc (South Jordan, Utah) under the trade name OpalDam™.

Clinical evaluation of OpalDam™ shows poor adhesion to the oral mucosa unless the underlying tissue surface is air-dried and kept free of saliva prior to application of the barrier. In addition, the cured barrier is rigid, which results in frequent detachment of the cured barrier during lengthy dental procedures (such as power bleaching, which employs a heat or light source to assist in the tooth bleaching process). Barrier failure (detachment) can result in contact of the underlying soft tissue with potentially harmful dental agents (such as the high-strength hydrogen peroxide used in tooth bleaching procedures or phosphoric acid, used in acid-etching of tooth surfaces prior to bonding procedures). Yet another disadvantage of OpalDam™ is its high peak exotherm during the curing process. Although temperature detection and pain threshold limits vary from patient to patient, it is generally accepted that most individuals can tolerate temperatures up to about 126° F. on the oral mucosa for only short periods of time.

Another disadvantage of currently available dental "resin dams", as they are called, comes from the inclusion of low molecular weight monomers, such as triethylene glycol dimethacrylate, urethane dimethacrylate, and hydroxyethyl methacrylate. Low molecular weight monomers are known skin sensitizers and can penetrate quickly into the oral mucosa both before and after the composition has "cured." See, for example, Hemmer et al., Journal of the. *American Academy of Dermatology*, 35, 377–380 (1996); Toby et al., *Arch. Dermatol.* 120, 1202–1205 (1984); Kanerva et al., *Contact Dermatitis* 37, 255–258 (1997); Kanerva et al., *Contact Dermatitis* 28, 268–275 (1993); Kanerva et al., *Contact Dermatitis* 33, 84–89 (1995). Since a typical free radical polymerization of low molecular weight monomers will never proceed to 100 percent completion, there are always residual monomers that do not participate in the polymerization reaction and thus can leach out from the polymerized material to cause unwanted skin reaction and possible health problems.

U.S. Pat. No. 5,900,245 discloses barriers and coatings formed by polymerization of polymerizable materials on the surface of tissue. When formed, these barriers or coatings are compliant with the tissue, as well as adherent, i.e., are capable of conforming to the tissue. In order to attain bioadhesion to the underlying tissue, the compositions described by the inventors must be polymerized from the tissue surface up; that is, a polymerization initiator is first placed on the tissue surface, which is then contacted with a polymerizable composition. When polymerization is initiated, the reaction starts at the tissue surface and progresses through the bulk of the polymerizable composition until the polymerization process is complete. The inventors claim improved adhesive characteristics for their methods and products by process. The inventors do not disclose a means for placing a polymerizable composition on a tissue surface, curing said polymerizable composition in situ, and obtaining a cured, adherent material.

There is a need for compositions that can be placed on a tissue surface in an initial malleable state, allowed to conform well to the underlying tissue, and then subsequently cured to a final flexible bioadhesive. Also, there is a need for a bioadhesive that has excellent bioadhesive qualities and that is flexible. Moreover, there is a need for a curable composition that forms a bioadhesive on a tissue surface upon curing and that does not generate much heat during the curing process, thus providing for patient comfort during the curing process. Finally, there is a need for a bioadhesive that can actively adhere well to both wet and dry tissue surfaces, obviating the need for extensive tissue preparation prior to application.

SUMMARY OF THE INVENTION

These and other objectives are achieved by the present invention, which provides low peak exotherm curable compositions which comprise a curable unsaturated compound, a curing agent and an adhesion promoter, and wherein the composition has a peak exotherm of less than about 50° C. (120° F.).

In one embodiment of the invention, the invention provides a composition which comprises a curable unsaturated compound, a curing agent and an adhesion promoter, wherein curing takes place with a peak exotherm of less than about 50° C. (120° F.).

In another embodiment of the invention, the invention provides a composition which comprises a curable unsaturated compound and a curing agent and wherein curing takes place with a peak exotherm of less than about 50° C. (120° F.).

Another embodiment of the invention provides a two part composition which comprises a first part comprising a curable polymerizable compound comprising unsaturated groups, an adhesion promoter and a curing agent, and a second part comprising a curable polymerizable compound comprising unsaturated groups, and a adhesion promoter, and a curing agent synergist of the curing agent of the first part, and wherein upon mixing of the first part and the second part curing takes place with a peak exotherm of less than about 50° C. (120° F.).

In another embodiment, the invention provides a method for forming a flexible bioadhesive on a tissue, comprising contacting the tissue surface with a composition comprising a curable unsaturated compound, a curing agent and an adhesion promoter, wherein the composition has a peak exotherm during curing of less than about 50° C. (120° F.), and curing the composition to form the flexible bioadhesive on the tissue.

Another embodiment of the invention is a flexible bioadhesive on a tissue surface prepared by contacting the tissue with a composition of the invention and then curing the composition to form the flexible bioadhesive on the tissue.

The compositions of the invention are (1) curable, i.e., can be transformed from a first liquid, gel, paste, or otherwise shapeable or malleable form to a second solid or otherwise rubbery form, (2) form bioadhesives to the underlying living tissue after curing has occurred, (3) do not generate heat in excess of that which is tolerable by or damaging to the living organism during the curing process, and (4) provide a bioadhesive after curing that is sufficiently flexible to conform to the movements of the underlying living tissue during the period of time which the bioadhesive is in use.

DETAILED DESCRIPTION OF TIE INVENTION

In one embodiment, the present invention is directed to curable compositions that have low peak exotherms. The compositions of the invention, after curing, are useful as bioadhesives. The bioadhesives of the invention, prepared by curing the compositions of the invention, are flexible. In another embodiment of the invention, the invention provides a method for forming a bioadhesive on a tissue by curing the compositions of the invention on the tissue.

In a preferred embodiment of the invention, the invention is directed to a composition comprising a blend or mixture of a curable component, an adhesion promoter, and a curing agent that upon curing has a low peak exotherm and when cured is a flexible bioadhesive. The curable component is capable of being cured from an initial rubbery state, for instance, a liquid, gel, paste, or putty, to a final non-rubbery state such as a flexible solid. The adhesion promoter is preferably a water-soluble or water-swellable polymer that is substantially insoluble in the curable component, and dispersed throughout it in a finely divided (powdered or granular) form. The adhesion promoter is thus included as a plurality of solid particles suspended in a liquid, gel, paste or semi-liquid matrix. The curing agent component comprises one or more compounds capable of initiating and propagating a curing reaction in the curable component. The curing reaction causes the compositions of the invention to change from an initial malleable state to a final flexible solid.

The invention solves the problem of there being too much heat generated in curing reactions by providing compositions that during the curing reaction have a low peak exotherm. Many curing reactions, such as the free-radical polymerization of acrylate and methacrylate monomers, generate heat as a result of the energetics of bond formation. Each bond that is formed results in a net increase in the temperature of the polymerizing mass, resulting in an initial increase in temperature that peaks at some finite point, the peak exotherm, after the initiation of polymerization. After the peak exotherm is reached, the polymerization process may still proceed, but it cannot sustain any further increase in the bulk material temperature. The polymerization process effectively ends when either all of the unsaturated groups have been used up or the unsaturated groups are constrained within a polymer network that prevents them from participating in any further reactions.

In another embodiment of the invention, compositions are provided which contain a drug or active ingredient and that can be placed on and allowed to conform to a tissue surface and then subsequently cured on the tissue surface to become a bioadhesive. The properties of the resulting bioadhesive allow it to remain adherent to and compliant with the underlying tissue, which allows for the effective migration of the contained drug or active ingredient into the underlying tissue over a long period of time.

In a preferred embodiment of the invention, the invention provides a method of forming a bioadhesive on a tissue. The method comprises applying compositions of the invention to a tissue surface, allowing them to conform to the underlying substrate, and subsequently curing them in situ. The method comprises placing the compositions of the invention on the tissue surface and subsequently curing in situ to provide a flexible and compliant material that is adherent to the underlying tissue, i.e., a flexible bioadhesive. Such bioadhesives are adherent to the underlying tissue as a direct result of the flexibility and compliance of the cured material.

The cured compositions of the invention (i.e., bioadhesives of the invention) have a flexible and compliant character and are able to adapt to the underlying living tissue as it moves and provide for bioadhesive properties even in the absence of an adhesion promoter. This adhesion is accomplished through conformity to the tissue structure, rather than any specific chemical or physiochemical interaction. The uniquely flexible behavior of the bioadhesives of the invention enables them to have bioadhesive properties even without the direct physical or chemical interactions provided by the presence of an adhesion promoter. Thus, in one embodiment of the invention, flexible bioadhesives can be prepared without the presence of an adhesion promoter. Embodiments of the invention having an adhesion promoter provide bioadhesives that have an additional source of bioadhesion as compared to those that do not include an adhesion promoter.

In general exothermic refers to a process, event, or chemical reaction that gives off heat. For example, a chemical reaction, such as a polymerization reaction, that produces heat energy is exothermic. An exotherm is a graphical plot of the temperature increase exhibited by an exotherm reaction versus the time since the beginning of the reaction.

The exothermic reaction that occurs during a free radical or addition polymerization process generates heat that is given off by the bulk material undergoing polymerization. Each bond formation that occurs as a result of two unsaturated moieties combining to form a bond gives off a finite amount of heat (heat of reaction). Thus, the heat given off by the bulk material is a multiple of the heat of reaction for a single polymer bond formation, times the number of bonds formed. Since the bond formation occurs over time (the curing process), not all of the heat is given off at once. In general, it is observed that the bulk material exhibits a rapid rise in temperature to a peak exotherm, followed by a slower decrease after that point in time. The peak exotherm temperature is relevant to the inventive curable bioadhesive composition, due to its intended placement in contact with a biological surface. The biological surface may be damaged or may transmit pain signals if the exothermic reaction exhibited by a curing composition is too great.

Since polymerization peak exotherms can be sufficiently high to cause discomfort when in direct contact with living tissue, care must be taken to limit the peak exotherm to that which can be easily and comfortably tolerated.

The inventor has made the surprising discovery that by limiting the number of unsaturated moieties per a given molecular weight of curable unsaturated compound, the heat generated or released during curing can be reduced. Thus, the peak exotherm upon curing of the compositions of the invention is reduced. This achieves the goal of limiting any potential damage to the target tissue surface.

Peak exotherms determined herein are the highest temperature measured (during the exothermic curing reaction) by placing between 60 and 100 milligrams of a curable composition on a flat surface temperature probe with a surface area of about 0.05 square inches (28.4 square millimeters) and curing the composition. In this specification peak exotherms are provided in both the Celsius (° C.) and Fahrenheit (° F.) temperature scales. One skilled in the art would understand that different experimental conditions would obtain different peak exotherms and that for comparison with the compositions of the invention, the above technique and conditions should be employed.

As used herein, "bioadhesive" means capable of adhering to a biological substrate such as skin and mucosa, or other tissue. Bioadhesive can also mean a compound, material, or composition having such adhesion properties to biological structures. The term "adhesion promoter" means a specific ingredient added to a composition to promote better adhesion to tissue.

As used herein, "flexible" means compliant, rubbery, bendable, stretchable and/or otherwise deformable. For example, a thin slab of material with dimensions of about one inch by one inch and having a thickness of about 1 mm which can be displaced at least 45 degrees out of plane without material failure or breakage, preferably at least 90 degrees out of plane, and most preferably at least 120 degrees out of plane is considered flexible. Flexible also means compliant with tissue; a flexible material is one that is able to change in concert with the change in shape of the underlying tissue with which it is in contact. The compositions of the invention when cured are flexible.

As used herein, the term "curable" means capable of undergoing a physical change from an initial rubbery state to a final non-rubbery state.

As used herein "malleable" means shapeable, formable, moldable, or otherwise capable of being conformed to an underlying substrate shape, texture, or topography.

As used herein, a curable unsaturated compound is any compound or material that is capable of participating in a curing or polymerization reaction. Unsaturated scompound generally include aliphatic organic molecules having double bonds between carbon atoms.

As used herein, "tissue" refers to any biological structure of a living organism, including skin, mucosa, internal organs and structures, as well as hard, mineralized, or partially mineralized structures, such as bone, tendon, cartilage, enamel, dentin, and fingernails. Tissue surfaces can be outer or inner surfaces of any of the aforementioned structures.

As used herein, "water-soluble" means capable of being dissolved, in part or in whole, in water or other aqueous media.

As used herein, "water-swellable" means capable of absorbing, but not actually dissolving in, water or other aqueous media.

As used herein, "curing agent" means a compound or combination of compounds capable or initiating or propagating a chemical reaction that results in a composition's change of state from rubbery to non-rubbery.

As used herein, "monomer" means a curable compound with one or more polymerizable unsaturated moieties and a molecular weight less than 1000.

As used herein, "oligomer" means a curable compound with one or more polymerizable unsaturated moieties and a molecular weight of greater than or equal to 1000. The terms "prepolymer" and "oligomer" are used in this specification to mean the same type of compound.

As used herein, "polymerize" means to undergo a chemical reaction that results in the formation of higher molecular weigh compounds from lower molecular weight unsaturated compounds.

The inventive compositions may be provided in either single- or multiple-part forms. Single-part compositions are preferred since no mixing is required prior to use. Formulating with curing agents that are photoactive is one means of curing single-part compositions. Preferably photoactive single-part compositions are packaged in light-resistant containers, such as black plastic syringes that are opaque to light.

Two-part compositions can be cured by providing a first part containing a curing agent (such as benzoyl peroxide) and a second part containing a curing agent synergist (such as N,N-dimethyl-p-toluidine). The first and second part are kept separated from one another until application to prevent premature curing (i.e., polymerization). Preferably, the first and second parts are packaged separately prior to use and mixed together just prior to application to the tissue surface. Two-part compositions of the present invention can be packaged in separate chambers of a dual chamber tube or syringe, pushed simultaneously out of the syringe with a dual barreled plunger into an attached static mixing device, whereupon the two parts will mix prior to exiting said static mixing device. The mixed composition that exits the static mixing device will now contain both compounds of the curing agent, and the curing reaction will begin. Preferably, the mixed composition is rapidly placed upon a tissue surface to form a bioadhesive of the invention.

Whether packaged as a single-part composition that requires no mixing prior to application or as a two-part composition that can be mixed just prior to application (as described above), the inventive composition may be applied to a tissue surface by any available and convenient means.

The compositions of the invention can be applied as a liquid, gel, paste or putty that is shaped or is allowed to shape itself to conform to the underlying tissue surface. Once the desired shape, conformation and sufficient coverage is attained, the composition can be cured. A particular advantage provided by one-part compositions that are cured by exposing them to actinic radiation (in general, light energy) is that the curing reaction can be delayed until it is assured that conformation to the underlying tissue surface is attained.

After curing the compositions of the invention on a tissue surface, the compositions of the invention become bioadhesives which adhere to the surface in order to provide short, medium, or long-term contact for the purpose of releasing a medicinal substance from the cured composition or acting as a protective physical barrier for the underlying tissue. The bioadhesives of the invention, prepared from the compositions of the invention, retain a degree of flexibility that allows them to adjust to changes in the underlying shape or conformation of the tissue. The flexibility and bioadhesion provided by the bioadhesives of the invention enables them to remain in full and intimate contact with tissue, even while the tissue, such as skin, changes shape as the organism moves, i.e., as a result of underlying joint, muscular, or tissue movement.

The following Table 1 represents, in general, the percentage range of curable bioadhesive compositions found to be most suitable. It is not intended to be limiting in its scope, but rather generally descriptive in nature.

TABLE 1

| Ingredient | Percent (w/w) |
| --- | --- |
| Curable unsaturated compound | 25–98 |
| Curing agent | 0.01–5 |
| Adhesion promoter | 10 . 50 |
| Non-curable diluent (optional) | 0–50 |

Curable Unsaturated Compounds

The curable unsaturated compounds of the compositions of the invention can be any compound (molecule), chemical, or mixtures thereof that are capable of undergoing a polymerization reaction. Preferred curable unsaturated compounds have a molecular weight greater than or equal to 1000, contain one or more unsaturated moieties and are capable of being polymerized. The preferred polymerizable moieties are unsaturated groups (methacrylate, acrylate, vinyl, etc.) present either in monofunctional form (a single polymerizable group per molecule) or multifunctional form (two or more polymerizable groups per molecule). To reduce the amount of heat generated during the curing process, preferred compositions of the invention reduce the average number of unsaturated groups per weight of composition by choosing relatively high molecular weight monofunctional or multifunctional constituents.

The curable unsaturated compounds of the invention can be any mono-, di-, tri-, or multi-functional unsaturated compound, or mixture thereof, capable of being polymerized through a free radical and/or addition polymerization reaction. The preferred unsaturated moiety is a methacrylate group, although any biologically acceptable compound containing an unsaturated moiety capable of participating in a polymerization reaction can be used in the compositions of the invention.

Methacrylate-containing compounds are preferred, due to the fact that they are generally less sensitizing (capable of inducing skin allergies) than acrylate and vinyl containing compounds. The most preferred curable unsaturated compounds are linear, end-capped dimethacrylate oligomers with molecular weights greater than or equal to 1000.

The compositions of the invention preferably comprise less than about 40 percent of a monomer or mixture of monomers. More preferably the compositions of ram the present invention are substantially free of monomers. Substantially free of monomers means that the compositions of the invention have less than about 30% by weight of a monomer or a mixture of monomers, preferably less than about 20% by weight of a monomer or a mixture of monomers, more preferably less than about 10% by weight of a monomer or a mixture of monomers, and even more preferably less than about 5% by weight of a monomer or a mixture of monomers.

Monomers (curable unsaturated compounds with molecular weights less than 1000) tend to contribute to high peak exotherms, are generally much more sensitizing to the skin and mucosal surfaces than their higher molecular weight oligomeric counterparts. In addition, when employed in oral or dental applications low molecular weight monomers tend to contribute undesirable tastes due to leaching and migration of monomer from the cured material.

Completely monomer-free compositions are contemplated to be within the scope of the present invention and are described in a number of the examples to follow. Monomer-free composition are the most preferred compositions of the invention. Monomer-free compositions do not have any monomers present.

Most preferably, the curable unsaturated compounds of the compositions of the invention are multifunctional oligomers containing no more than about one unsaturated moiety (preferably a methacrylate moiety) per 500 of molecular weight. The preferred curable unsaturated compounds can therefore be described by the numeric representation of their molecular weight per unsaturated moieties. This numeric representation of the molecular weight of the curable unsaturated compound per unsaturated moiety is defined herein as an unsaturation index.

The unsaturation index is defined herein as the molecular weight of an unsaturated compound divided by the number of unsaturated moieties or groups. For example, a curable unsaturated compound having a molecular weight of 1000 and two methacrylate moieties would have an unsaturation index of 500 (1000 divided by 2). Two methacrylate groups in a curable unsaturated compound with a molecular weight of 1700 would yield an unsaturation index of 850 (1700 divided by 2). Three methacrylate groups in a curable unsaturated compound with a molecular weight of 2400 would have an unsaturation index of 800 (2400 divided by 3). Preferred curable unsaturated compounds of the invention have an unsaturation index (as defined herein) greater than or equal to 500. More preferred unsaturated compounds of the Pa invention have an unsaturation index of from about 600 to about 1500. Most preferred unsaturated compounds of the invention have an unsaturation index of from about 600 to about 1000.

It should be noted that an average composition unsaturation index can be affected by the inclusion of saturated compounds, additives or diluents in addition to the curable unsaturated compound. For example, if the unsaturation index of a curable unsaturated compound is 600, but the composition is further diluted by the inclusion of a saturated diluent at 50 percent w/w, the resulting formulation will have an overall composition unsaturation index of 1200 (600 divided by 0.50). Thus, saturated compounds, additives and diluents may be used to increase the unsaturation index.

Particularly preferred oligomers are dimethacrylates ranging in molecular weight from 1,000 to about 3,000. Dimethacrylate polyetherurethane oligomers commercially available from Echo Resins, Inc (Versailles, Mo.) under the trade names MLU-340, MLU-341, and MLU-342 are preferred oligomers for the invention.

Adhesion Promoters

Preferred curable compositions of the invention comprise an adhesion promoter. Adhesion promoters are included in the compositions of the invention to improve the adhesion of the cured composition to biological tissues. Adhesion promoters are compounds or substance that improve the peel or grab strength, to the contacted biological surface, of the bioadhesive resulting from the curing of the compositions of the invention. The chemical nature of the adhesion promoter can be selected for the best bioadhesion to a particular tissue, since tissues will vary in their surface properties. For example, a moist mucosal surface can require a different adhesion promoter than a relatively dry skin surface.

Preferred bioadhesives of the invention, formed by the curing of the preferred curable compositions of the invention attach well to wet field surfaces. Thus, the preferred bioadhesives of the invention are especially useful in dental applications, since it has been found that the bioadhesives of the invention are particularly adherent to wet field tissue surfaces such as the oral mucosa.

Preferably, in preparing compositions of the invention which include an ahesion promoter, all of the components (other than the adhesion promoter) are combined to form a curable composition or matrix. The adhesion promoter is then added to form the final composition of the invention. Most preferably, the adhesion promoters are dispersed, but not actually dissolved, in the curable composition in a finely divided form.

Preferred adhesion promoters include, for example, finely divided poly(acrylic acid), poly(ethylene oxide), poly(vinyl pyrrolidone), poly(maleic anhydride-co-methyl vinyl ether), karaya gum, guar gum, acacia gum, carboxypolymethylene, chitosan, hydroxyethyl cellulose, sodium carboxymethylcellulose, hydroxypropyl cellulose, polycarbophil, poly(vinyl alcohol), hydroxypropylmethyl cellulose, and the like. Other high molecular weight synthetic and natural water-soluble or water-swellable polymers can also be used as adhesion promoters. Combinations of adhesion promoters can be used when compatible with each other. Compatibility means that two or more adhesion promoters can be used in combination without sacrificing or reducing the bioadhesive properties of the cured composition in contact with a tissue surface. More preferred adhesion promoters are polycarbophil with a molecular weight in excess of about 100,000. Most preferred adhesion promoters are polycarbophil with a molecular weight in excess of about 1,000,000.

Curing Agent

Curing agents of the compositions of the invention include both light- and heat-activated polymerization catalysts. Any compound capable of being induced, either through the application of an outside energy source or through the combination (at the time of use) of two or more composition components, to initiate a polymerization reaction can be used in the compositions of the invention as a curing agent. Preferred curing agents are photoinitiators that are capable of initiating a polymerization reaction upon exposure to light energy. More preferred curing agents are photoinitiators that are capable of initiating a polymerization reaction upon exposure to specific wavelengths of light energy in the visible, near infrared or ultraviolet spectrum. Examples of photoinitiators useful with the compositions of the invention include camphorquinone, benzoin methyl ether, benzoin ethyl ether, benzoin butyl ether, 2-hydroxy-2-methyl-1-phenyl propane-1-one, oligo[2-hydroxy-2-methyl-1-[4-(1-methylvinyl)phenyl] propanone], benzildimethylketal, 2-isopropylthioxanthone, 4-isopropylthioxanthone, benzophenone (and derivatives), 9,10-anthraquinone, 1-hydroxycyclohexyl phenyl ketone, and the like, and combinations (where compatible) thereof. Certain curing agents require the presence of a curing agent synergist (within the composition either at the point of manufacture or added to the composition at the time of use). A curing agent synergist may act, along with the curing agent, to initiate the polymerization reaction chemically within the composition, without the use of an outside energy source such as heat or light. Particularly useful curing synergists are amine compounds. A curing agent synergist may also accelerate a photoinitiated polymerization reaction. Specific examples of curing agent synergists are dimethylaminoethyl methacrylate, N,N-dimethyl-p-toluidine, and ethyl-4-dimethylamino benzoate.

Non-curable Diluent

The increase in the molecular weight of the curable unsaturated compound or compounds used in the compositions of the invention often results in the concurrent increase in the viscosity of the bulk material. Preferred compositions of the invention comprise a non-curable diluent. In order to formulate a material that can be readily shaped into a desired form (such as a thin film on the surface of gingival tissue in the mouth), the viscosity of the inventive composition must be low enough so that it may be, for instance, easily pushed by a plunger mechanism from a syringe. The compositions of the invention preferably comprise a non-curable diluent capable of dissolving the curable unsaturated compound, thereby resulting in a mixture that has a workable, extrudable, malleable, or otherwise formable consistency.

Thus, if the viscosity rises above that which is suitable for manipulation, i.e., extrusion, shaping, and forming the composition prior to curing, a diluent should be included in the curable compositions of the invention to reduce the composition's viscosity to a range that may be manipulated.

One way of reducing the working viscosity of curable compositions is to use lower molecular weight unsaturated diluents. This approach is not preferred because it would lead to an increase in the composition peak exotherm due to an increase in the number of unsaturated moieties. Thus, it is preferred that a saturated or otherwise non-polymerizable diluent be used to reduce the working viscosity of the present inventive compositions.

Low molecular weight unsaturated monomers are preferably kept to a minimum in the compositions of the invention for the additional reasons, especially in the context of oral or dental applications, that they have a detectable and often unpleasant taste. Low molecular weight monomer leaching from the cured composition, since there is inevitably at least a small amount of monomer that does not polymerize during a free radical curing reaction, leads to unacceptable organoleptic properties.

Non-curable diluents (hereinafter referred to as merely diluents) that have utility in the preparation of the inventive compositions must be able to dissolve and thereby reduce the viscosity of the curable unsaturated oligomer. The diluent should therefore have a viscosity that is lower than that of the curable unsaturated oligomer at room temperature. Generally speaking, preferred diluents are liquids. Suitable diluents also should have a low level of toxicity for their intended use. Preferred diluents are not easily extracted from the inventive composition after curing. For example, when in contact with the moisture in saliva. Therefore, preferred diluent for bioadhesives used in oral applications are preferably water-insoluble. Preferred diluents have a viscosity range of from about 1 centipoise to about 2000 centipoise. The viscosity of a diluent can be measured with a Brookfield RVT DVII+ Viscometer (Brookfield Engineering, Middleboro, Mass.) at 25° C., using cylindrical spindle #4 at a spindle speed of 5 rpm. A particularly preferred diluent is capric/caprylic triglyceride.

Suitable non-curable diluents include solvents, plasticizers, emollients, and a broad range of liquid ester compounds (the reaction product between an acid and an alcohol). The type of non-curable diluent, as well as its concentration in the final composition, will be dependent upon the oligomer selected. Whereas one non-curable diluent may be a suitable solvent for an oligomer with a molecular weight of 1500, that same diluent may not be a suitable solvent for an oligomer with a molecular weight of 4000. The oligomer should be soluble in the non-curable diluent chosen.

Non-curable diluents include, for example, triglycerides such as capric/caprylic triglyceride, liquid mono- and diglycerides, vegetable oils such as avocado oil, safflower oil, olive oil, and sweet almond oil, and other similar compounds.

Auxiliary Components

The inventive curable bioadhesive composition may also contain a pigment or dye in order to allow for ease of visual placement and detection, in addition to providing a means to physically block out radiant energy from heat and light sources that are frequently employed to accelerate, for instance, tooth whiteners. Pigments such as titanium dioxide and zinc oxide, are preferred, but any opacifying or light-attenuating pigment, dye, or insoluble particle may be used. Pigments or dyes may optionally be added to the composition in an amount from about 0.0001 percent to about 10 percent by weight of the composition.

Preferred light attenuating pigments are titanium dioxide (all particle sizes, include nanometer-sized powder particles) and zinc oxide (also all particle sizes, including nanometer-sized powder particles). Polymer particles, such as those from finely ground high density polyethylene and poly (tetrafluoroethylene), are also useful as light attenuating ingredients in the curable compositions. They may also be used as "extenders", in order to even further reduce the peak exotherm (by occupying "space" in the formulation as a non-curable solid filler).

Pigments and dyes suitable for use in the compositions of the invention are compounds that are biologically acceptable, for example, in the oral cavity or on the surface of the skin.

Other auxiliary components include, for example, fragrance and flavor additives, preservatives, antimicrobial agents, active drugs and medicaments. Inhibitors, such as hydroquinone methyl ether (MEHQ), hydroquinone (HQ) and butylated hydroxytoluene (BHT) may be added to the compositions in order to prevent premature polymerization before the time of use. Skin and mucosal penetration enhancers, such as glyceryl triacetate (triacetin) can also be included, especially when enhanced diffusion of a drug or active ingredient into tissue is desired.

Bioadhesion Synergists

Surprisingly, it was found that certain compounds containing divalent metal ions, such as zinc oxide and dicalcium phosphate anhydrous, increased the bioadhesive strength of the inventive compositions when used in conjunction with adhesion promoters that contain carboxylic acid or anhydride group functionality. Thus, the combination of a carboxylic acid or anhydride-functional adhesion promoter with a divalent metal ion-containing compound resulted in an unexpected increase in the bioadhesion of the compositions of the invention after curing.

While not wishing to be bound by any particular theory, it is hypothesized that upon contact with moisture, the carboxylate moieties of the adhesion-promoting polymer create a low pH environment at the interface between the bioadhesives of the invention. This low pH environment is conducive to the solubilization of, for example, zinc oxide, thereby releasing divalent zinc ions into the interfacial environment. The available zinc ions may create crosslinking between intermingling polymer chains, particularly on mucosal surfaces that contain high molecular weight mucins. Increased crosslinking between adhesion promoter polymer chains and tissue surface polymer chains may account for the improved adhesion at the interface between the bioadhesives of the invention (the cured compositions of the invention) and the underlying biological substrate.

Alternatively, while not wishing to be bound by theory, it is hypothesized that divalent cations shield the charges provided by carboxylate moieties and thereby enable the bioadhesive to conform more closely to the tissue surface by reducing charge-charge repulsion between carboxylate groups.

Thus, divalent or multivalent metal ion compounds that are insoluble in the curable composition, or cured composition resulting in the bioadhesives of the invention can be used in the compositions of the invention. These compounds are called adhesion promoter synergists. In particular, compounds containing zinc, calcium, magnesium, or other divalent or multivalent metal ions cause an unexpected increase in the adhesive properties of the bioadhesives of the invention that also contain at least one polymer having pendant carboxylic acid or anhydride moieties. In other words, an adhesion promoter comprising at least one polymer having pendant carboxylic acid or anhydride groups in combination with at least one divalent or multivalent metal ion-containing compound has been found to have surprising utility in the present curable compositions of the invention.

Although not exhaustive, a list of divalent compounds suitable for use with at least one polymer having pendant carboxylic acid or anhydride groups includes zinc acetate, zinc aspartate, zinc benzoate, zinc carbonate, zinc chloride, zinc citrate; zinc cysteinate, zinc gluconate, zinc glutamate, zinc lactate, zinc laurate, zinc myristate, zinc palmitate, zinc phenolsulfonate, zinc stearate, zinc sulfate, zinc undecylenate, calcium acetate, calcium ascorbate, calcium aspartate, calcium benzoate, calcium carbonate, calcium chloride, calcium citrate, calcium dihydrogen phosphate, calcium disodium ethylenediaminetetraacetate, calcium fluoride, calcium gluconate, calcium glycerophosphate, calcium hydroxide, calcium lactate, calcium laurate, calcium monofluorophosphate, calcium myristate, calcium pantothenate, calcium paraben, calcium phosphate, calcium propionate, calcium pyrophosphate, calcium saccharin, calcium salicylate, calcium silicate, calcium sorbate, calcium stearate, calcium sulfate, calcium tartarate, calcium undecylenate, magnesium acetate, magnesium aluminum silicate, magnesium ascorbate, magnesium ascorbyl phosphate, magnesium aspartate, magnesium benzoate, magnesium carbonate, magnesium chloride, magnesium fluoride, magnesium fluorosilicate, magnesium gluconate, magnesium glycerophosphate, magnesium hydroxide, magnesium myristate, magnesium oxide, magnesium palmitate, magnesium propionate, magnesium salicylate, magnesium silicate, magnesium sodium fluorosilicate, magnesium strearate, magnesium sulfate, and the like.

The following Examples serve to provide further illustration of the invention by are not meant in any way to restrict the effective scope of the invention.

EXAMPLES

Example I

The following composition is useful for isolating gingival tissue in the oral cavity from therapeutic agents, such as oxidizing tooth-whitening compositions. Such oxidizing compositions are placed on the tooth enamel surface for a period of time from about 5 minutes to about 2 hours, or until the desirable degree of tooth whitening is achieved. When cured, the present inventive composition protects the soft gingival tissue from the possible harmful effects of the tooth whitening composition.

Composition 1A

| Ingredient | Function | Percent (w/w) |
|---|---|---|
| Methacrylated polyetherurethane oligomer (MW 1200) | Curable unsaturated compound | 50.178 |

-continued

Composition 1A

| Ingredient | Function | Percent (w/w) |
|---|---|---|
| Capric/caprylic triglyceride | Non-curable diluent | 22.374 |
| Polycarbophil | Adhesion promoter | 25.000 |
| Pyrogenic silica | Thickener | 2.000 |
| Camphorquinone | Photoactive curing agent | 0.100 |
| Ethyl-4-dimethylamino benzoate | Curing agent synergist | 0.348 |
| TOTAL | | 100.000 |

The above composition was prepared in a "light safe" room, where all ambient light sources were filtered in order to remove any spectral component below 500 nanometers (nm). This precaution is necessary, due to the absorption peak for this particular composition's photoactivator (camphorquinone), which has an absorption maximum of 466-nm. Unfiltered light that included the 466-nm spectral component range would cause premature polymerization of the composition prior to placing it in light safe packaging.

The curing agents (camphorquinone and ethyl-4-dimethylamino benzoate) were dissolved in the capric/caprylic triglyceride diluent. This mixture was then combined with the oligomer in a vacuum mixer, along with the silica thickener. The components were mixed together, initially without drawing a vacuum in the mixing vessel, until a homogeneous mixture was obtained. Subsequently, 20" Hg of vacuum was drawn in the mixing vessel for a period of 5 minutes, whereupon a mixture free of entrapped air bubbles was obtained. It should be noted that excessive mixing under a vacuum is not recommended for compositions containing unsaturated moieties. This is due to the propensity for unsaturated compounds to undergo premature polymerization when deprived of oxygen ($O_2$), which acts in synergy with typical polymerization inhibitors such as hydroquinone methyl ether (MEHQ), hydroquinone (HQ) and butylated hydroxytoluene (BHT).

The finished composition above was then packaged into opaque, black 3-gram plastic syringes under light-safe conditions. The finished composition was an off-white, opaque gel that could be easily extruded from the syringes. The opacity of the product most likely resulted from the insolubility of the polycarbophil particles in the curable matrix, since a composition prepared in a similar fashion to Example I above that did not include the polycarbophil was a transparent gel with a slight yellow color.

A modified version of the inventive composition above was prepared that showed greater opacity due to the addition of zinc oxide.

Composition Ib

| Ingredient | Percent (w/w) |
|---|---|
| Methacrylated polyetherurethane oligomer (MW 1200) | 41.652 |
| Capric/caprylic triglyceride | 33.400 |
| Polycarbophil | 20.000 |
| Pyrogenic silica | 1.500 |
| Camphorquinone | 0.100 |
| Ethyl-4-dimethylamino benzoate | 0.348 |
| Zinc oxide | 3.000 |
| TOTAL | 100.000 |

Example II

A peak exotherm was determined, in accordance with the following procedure, for the composition prepared in Example Ia.

The peak exotherm attained was determined using a standardized test procedure that accurately duplicates the in-use placement, thickness, and curing conditions that one would employ in situ. The method comprised the use of a flat surface disc thermoprobe with a detection surface diameter of 0.31 inches, a response time of 0.75 seconds, and a time constant of 0.15 seconds. The probe was connected to a digital J-type thermocouple thermometer (Digisense Type-J Thermometer, Cole-Palmer Corporation, Vernon Hills, Ill.). A large enough bead of the above composition was placed on the detection disc in order that the entire probe surface was covered with the curable material. The bead of material was then cured using a hand-held dental curing light (Optilux 500, Demetron Corporation, Danbury, Conn), the fiber optic probe of which was positioned (with the help of a plastic spacer) 5-mm away from the top of the material bead. A timer was used to determine the time at which the peak exotherm was attained, along with the digital readout from the thermometer. An average of three measurements was used to determine the peak exotherm under the conditions of the test. The above composition bead cured to a solid, flexible bead that resisted permanent deformation when manipulated by hand. The peak exotherm attained occurred at 23 seconds after the start of light exposure and was 40.6° C. (105° F.).

The highest point on the material bead was measured to be approximately 2 millimeters (mm), which approximates the thickness (1 to 2 mm) that can be practically applied onto the gingival surface without causing excessive material buildup. It is important to somewhat overestimate the volume of material that may be in contact with the biological surface, in order that a peak exotherm for the material be estimated that greatly exceeds safety parameters. It is generally accepted that a maximum temperature of 53.4° C. (128° F.) in the oral cavity is tolerated by most subjects; higher temperatures usually result in patient discomfort. In the interest of providing a wide margin of safety, it is preferred that the peak exotherm for the inventive compositions, determined in accordance with the test method outlined above, not exceed 50° C. (120° F.), and preferably not exceed 43.4° C. (110° F.). Most preferably, the peak exotherm is less than or equal to 40° C. (104° F.).

A commercially available curable gingival isolation material (OpalDam™, Ultradent Products, Inc., South Jordan, Utah) was obtained and tested in accordance with the above procedure. The commercial material bead reached its peak exotherm 26 seconds after the start of light exposure and the peak exotherm was 124° F. The resulting material was a brittle solid that did not possess the flexural properties that would allow it to "give" along with minor movement that may occur in the underlying gingival tissue. Rigidity in the final cured composition is more likely to cause separation of the material from the gingival tissue, resulting in, for instance, bleaching agent leakage and possible damage to the tissue underlying the gingival barrier.

A further comparison of the peak exotherms of several different compositions was performed. Table 2 below shows general properties of the monomers and/or oligomers used to prepare the compositions, which are further described in Table 3.

TABLE 2

| Monomer/Oligomer | MW | No. of Unsaturated Groups | Unsaturated Group Type | UI |
|---|---|---|---|---|
| Urethane Dimethacrylate | 470 | 2 | Methacrylate | 235 |
| Ethoxylated BisGMA | 540 | 2 | Methacrylate | 270 |
| MLU-340 | 1200 | 2 | Methacrylate | 600 |

MW = Molecular weight
UI = Unsaturation Index (MW divided by the # of Unsaturated Groups)

| | Amount (w/w) | | |
|---|---|---|---|
| Ingredient | Composition II a | Composition II b | Composition II c |
| Urethane Dimethacrylate | 99.55 | | |
| Ethoxylated BisGMA | | 99.55 | |
| MLU-340 | | | 99.55 |
| Camphorquinone | 0.10 | 0.10 | 0.10 |
| Ethyl-4-dimethylaminobenzoate | 0.35 | 0.35 | 0.35 |
| TOTAL | 100.00 | 100.00 | 100.00 |

Peak exotherms for the compositions IIa, IIb, and IIc above were determined in accordance with the procedure outlined above. The results are shown in Table 3 below, and clearly demonstrate the superior limited exothermic properties of Compositions Ia, Ib and II c, which are representative of the inventive compositions.

TABLE 3

| Composition | Start Temp (° C.) | Peak Temp (° C.) | Δ Temp (° C.) |
|---|---|---|---|
| II a | 23.5 | 65.8 | 42.3 |
| II b | 22.5 | 61.6 | 39.1 |
| OpalDam ® | 22.9 | 51.2 | 28.3 |
| II c | 23.2 | 46.8 | 23.6 |
| Ia | 23.4 | 40.6 | 17.2 |
| Ib | 22.7 | 33.4 | 11.0 |
| None (curing light only) | 22.4 | 51.0 | 28.6 |

The following composition was clinically tested for its general properties as a gingival barrier material during a light-activated tooth whitening procedure. Zinc oxide was added to increase the opacity of the cured composition in situ; the increased opacity reduced the amount of light that could penetrate through the gingival barrier during the tooth whitening procedure. The composition below was prepared in a manner similar to that in Example I. The final compositions was placed in 1-cc black syringes and stored at room temperature until use.

| Composition III | |
|---|---|
| Ingredient | Percent (w/w) |
| Methacrylated polyetherurethane prepolymer (MLU-340) | 41.652 |
| Capric/caprylic triglyceride | 33.400 |
| Polycarbophil | 20.00 |
| Fumed silica (Cab-O-Sil M5) | 1.500 |
| Camphorquinone | 0.100 |

-continued

Composition III

| Ingredient | Percent (w/w) |
|---|---|
| Ethyl-4-dimethylamino benzoate | 0.348 |
| Zinc oxide | 3.000 |
| TOTAL | 100.000 |

Four volunteer subjects were used to compare the in situ properties of the above composition to those of a commercial light-cured resin dam. The composition of the invention was applied to the left half of the mouth, on both the upper and lower gingival margins, while the commercial resin dam was applied to the right half of the mouth in exactly the same fashion. The procedure was performed as follows: a plastic syringe tip was attached to the Leur-lock end of either a syringe of the above formulation or a syringe of the commercial resin dam. Material from each respective syringe was applied carefully along the margin between the gingiva and the tooth enamel of one half of the upper (maxillary) teeth. The same process was repeated for one half of the lower (mandibular) teeth. While the composition of the invention had flow properties that allowed for the entire half arch to be coated prior to curing with the dental curing light, the commercial resin dam tended to flow too easily, resulting in the need to cure the material every so often to prevent the material from flowing down and covering the hard surface of the tooth. The test materials were left in place during a tooth whitening procedure that lasted, depending upon the subject, between 20 and 60 minutes.

The subjects noted that the composition of the invention was more comfortable for several reasons. First, the subjects noted that the composition of the invention produced less heat than the commercial resin dam material. Second, the composition of the invention did not have the bitter taste that they identified as originating from the commercial resin darn. The dental professionals performing the procedure noted less gingival irritation after 60 minutes (the duration of the tooth whitening procedure), resulting from the higher opacity of the inventive composition, together with its reduced peak exotherm. Importantly, the dental professionals noted that removal of the cured composition of the invention following the tooth whitening procedure was much more comfortable for the subjects than the OpalDam™, due to the fact that it came out of undercuts better and was more flexible.

Example IV

A demonstration of the flexibility of the inventive compositions in comparison to prior art compositions was conducted. Representative compositions of the invention were prepared as in the other examples. 1-mm thick cured fillets were prepared by placing uncured material between two glass microscope slides that were spaced apart from one another with two additional microscope slides, in such a manner as to create a rectangular mold. The first two slide were pressed together until material was spread through the mold and until they touched the spacer slides. The material was then cured for 3 minutes with a dental curing light, as described above. The resulting cured rectangular fillets were exactly 1-mm thick and varied tremendously in qualitative flexibility and hardness.

To compare flexibility, the fillets were securely positioned in a square edged clamp (one half of the fillet was clamped and the other half was free). The free half was slowly bent out of plane until the material failed and broke into two pieces. The approximate angle of deflection at which failure occurred was measured.

While the Compositions IIa, IIb, and the OpalDam® material failed between 45 and 75 degrees from plane, the inventive compositions I and IIc easily passed through the 90 degree out of plane mark and did not fail when folded virtually in half (the clamp prevented an angle greater than 160 degrees from plane being attained).

Example V

The bioadhesive properties of various compositions were evaluated qualitatively by coating the surface of the forefinger with saliva and immediately placing a curable composition on the wet surface. After 15 seconds, the composition was cured with a dental curing light for 60 seconds and the bioadhesive quality of the resulting cured mass determined by peeling slowly from the surface of the skin. In some instances (Compositions IIa and IIb), very little adhesion was observed, however, the compositions of the invention, Ia and IIc, were difficult to remove and held to the skin in a manner similar to very sticky tape. The Composition Ib was clearly superior to any of the other compositions. The commercial material, OpalDam®, did not adhere well to saliva moistened skin, but did adhere well to dry skin (this is consistent with the clinical observation that OpalDam® works well only in a dry field, i.e., if the mucosal surfaces have been air dried prior to contact with the curable material.

Example VI

Composition III was also tested for its ability to attenuate light energy. Since gingival barrier materials are often used during light-activated tooth whitening procedures, it is important that such materials be able to effectively reduce the amount of light energy that reaches the underlying tissue. Excess light energy that reaches the soft gingival tissue may cause damage in a manner similar to sunburn, which, if occurring in the oral cavity, can cause a tremendous amount of post-procedure pain for the patient.

Light attenuation by gingival barrier compositions was measured by taking a baseline measurement for a light source (in this case, a metal halide source transmitted to a light delivery construct through fiber-optic means) with a laser power meter (Ophir Model AN/2). The baseline measurement for the light source was 135 mW/cm$^2$. Two standard glass microscope slides were placed on top of one another and in the path between the light source and the power meter detector well. This measurement was taken in order to ascertain the light attenuation, if any, caused by the glass slides. The measurement was taken again and found to be the same, 135 mW/cm$^2$, thus indicating that the glass slides did not attenuate the light energy between the light source and the detector well.

A bead of Composition III was placed in the center of one of the glass slides and two cover slips were positioned as "spacers" prior to placing the second glass slide directly on top of the first one. The bead of material was spread into a thin film by pressing the slides together until the cover slip spacers would not allow further compression. Before and after measurements of the glass slides with and without the cover slip spacers showed the material film thickness to be about 100 microns (1/10 of a millimeter). The "sandwiched" material film was cured in place with a standard dental curing light for 60 seconds.

The cured 100 micron film, sandwiched between two glass slides, was then placed in the path between the light source and the power meter detector well. The meter now read 62 mW/cm$^2$, a reduction in power density of approximately 54%.

The same test performed on a commercial gingival isolation material (OpalDam™) resulted in a reading of 93 mW/cm$^2$, a reduction in power density of only 32%. The light-attenuating ability of Composition III was almost 70 percent higher than the commercial material.

Example VII

Additional compositions were prepared as follows, in accordance with the general manufacturing procedures outlined previously. These formulations are intended only to be representative and by no means limiting.

| | Compositions VIIa–VIIe | | | | |
|---|---|---|---|---|---|
| Ingredient | VIIa | VIIb | VIIc | VIId | VIIe |
| Oligomer 1 (MLU-340) | 41.652 | 41.652 | | | |
| Oligomer 2 (MLU-341) | | | 25.300 | | |
| Oligomer 3 (MLU-342) | | | | 30.000 | 30.000 |
| Capric/caprylic triglyceride | 33.400 | 33.400 | 41.000 | 45.552 | 49.552 |
| Polycarbophil | 20.000 | 20.000 | | | |
| Polyoxyethylene (High MW) | | | 25.000 | | |
| Polyvinylpyrollidone | | | | 20.000 | |
| Poly(methyl vinyl ether-co-maleic anhydride) | | | | | 15.000 |
| Fumed silica | 1.500 | 1.500 | 3.000 | 2.000 | 2.000 |
| Camphorquinone | 0.100 | 0.100 | 0.150 | 0.100 | 0.100 |
| Ethyl-4-dimethylamino benzoate | 0.348 | 0.348 | 0.550 | 0.348 | 0.348 |
| Dicalcium phosphate anhydrous | | 2.000 | | | |
| Zinc oxide | | | 5.000 | | 3.000 |
| Titanium dioxide | 3.000 | 1.000 | | 2.000 | |
| TOTAL | 100.000 | 100.000 | 100.000 | 100.000 | 100.000 |

Example VIII

To further demonstrate the advantages of utilizing an oligomer as the curable component in a representative inventive composition, a comparison of a formulation that contains an oligomer as its curable unsaturated compound (VIIIa) was compared to an identical that had as its only difference the use of a monomer (urethane dimethacrylate) as its curable unsaturated compound (VIIIb).

| Ingredient | Composition VIIIa | Composition VIIIb |
|---|---|---|
| Methacrylated polyetherurethane prepolymer (MLU-340) | 41.652 | |
| Urethane dimethacrylate | | 41.652 |
| Capric/caprylic triglyceride (Crodamol GTCC) | 33.400 | 33.400 |
| Poly(acrylic acid) (Noveon AA-1) | 20.000 | 20.000 |
| Fumed silica (Cab-O-Sil M5) | 1.500 | 1.500 |
| Camphorquinone | 0.100 | 0.100 |
| Ethyl-4-dimethylamino benzoate | 0.348 | 0.348 |
| Zinc oxide | 3.000 | 3.000 |
| TOTAL | 100.000 | 100.000 |

While the inventive Composition VIIIa demonstrated desirable low peak exotherm properties, Composition VIIIb reached a peak exotherm of 52 degrees C. (125 degrees F.). In addition, Composition VIIIb was extremely brittle, whereas Composition VIIIa was flexible. Thus, the compositions of the invention achieve both low peak exotherms and flexibility. This also demonstrates the advantage of using oligomers rather than monomers in bioadhesive compositions.

Example IX

A two-component curable composition suitable for use as a tissue sealant was prepared; the individual parts 1 and 2 were placed in separate chambers of a light resistant, dual-chambered syringe (Plas-Pak Industries, Norwich, Conn). The two components are mixed together as they are forced out of the syringe with a dual piston through a mixing baffle (also known in the art as a static mixer) attached to the exit end of the syringe, opposite the plunger. Upon being forced into one end of the static mixing chamber, the two components become mixed by the time they emerge from the other end. This particular static mixing chamber had 8 elements (which are like baffles or plates that direct the flow of the materials through the chamber), although other designs and numbers of elements are contemplated.

| Ingredient | Part 1 | Part 2 |
|---|---|---|
| Methacrylated polyetherurethane prepolymer (MLU-341) | 37.540 | 37.540 |
| Capric/caprylic triglyceride | 35.960 | 41.960 |
| Polycarbophil | 20.000 | |
| Poly(vinyl pyrrolidone) (K30) | | 18.000 |
| Fumed silica | 2.000 | 2.200 |
| Benzoyl peroxide | 0.500 | |
| N,N-dihydroxy-p-toluidine | | 0.300 |
| Dicalcium phosphate anhydrous | 4.000 | |
| TOTAL | 100.000 | 100.000 |

Although the invention has been described with references to preferred embodiments and examples thereof, the scope of the present invention is not limited to those described embodiments. Those skilled in the art will realize that further embodiments can be made without departing from the spirit of the invention, and it is intended to include all such further modifications, adaptations and changes as come within the scope of the claims set forth herein.

What is claimed is:

1. A composition comprising:
   a compound having an unsaturation index of at least about 500;
   a curing agent; and
   an adhesion promoter,
   wherein the composition is curable and has a peak exotherm of less than about 50° C. (120° F.).

2. A composition according to claim 1, further comprising a non-curable diluent.

3. A composition according to claim 1, wherein the curable unsaturated compound comprises at least one unsaturated group selected from the group consisting of methacrylate, acrylate, vinyl and combinations thereof.

4. A composition according to claim 3, wherein the unsaturated group is methacrylate.

5. A composition according to claim 1, wherein the curable unsaturated compound is an oligomer.

6. A composition according to claim 5, wherein the oligomer is a dimethacrylate oligomer.

7. A composition according to claim 6, wherein the dimethacrylate oligomer is a dimethacrylate polyetherurethane oligomer.

8. A composition according to claim 1, wherein the peak exotherm is from about 20° C. to about 45° C.

9. A composition according to claim 1, wherein the peak exotherm is from about 35° C. to about 40° C.

10. A composition according to claim 1, wherein the adhesion promoter is selected from the group consisting of poly(acrylic acid), poly(ethylene oxide), poly(vinyl pyrollidone), poly(maleic anhydride-co-methyl vinyl ether), karaya gum, guar gum, acacia gum, carboxypolymethylene, chitosan, hydroxyethyl cellulose, sodium carboxymethylcellulose, hydroxypropyl cellulose, polycarbophil, poly(vinyl alcohol), hydroxypropylmethyl cellulose and compatible combinations thereof.

11. A composition according to claim 1, wherein the adhesion promoter is polycarbophil.

12. A composition according to claim 1, wherein the curing agent is a photoinitiator.

13. A composition according to claim 1, further comprising a bioadhesion synergist.

14. A composition according to claim 13, wherein the bioadhesion synergist is a divalent metal or an alkali metal ion.

15. A composition according to claim 1, wherein after curing the composition is a flexible bioadhesive.

16. A composition according to claim 1, further comprising a curing agent synergist.

17. A composition according to claim 16, wherein the curing agent synergist is ethyl-4-dimethylaminobenzoate.

18. A composition according to claim 1, further comprising a silica thickener.

19. A composition according to claim 1, wherein the composition is substantially free of monomers.

20. A composition according to claim 1, wherein the composition is monomer free.

21. A composition according to claim 2, wherein the non-curable diluent has a viscosity of from about 1 centipoise to about 2000 centipoise.

22. A curable composition according to claim 1, further comprising a light-attenuating pigment.

23. A curable composition according to claim 22, wherein the light-attenuating pigment is selected from the group consisting of titanium dioxide and zinc oxide.

24. A composition according to claim 22, wherein the light-attenuating pigment is present from about 0.0001 percent to about 10 percent by weight of the composition.

25. A two part system comprising:
a) a first part which comprises a curing agent; and
b) a second part which comprises a curing agent synergist of the curing agent of the first part,
wherein the first part or the second part or both further comprises a compound having an unsaturation index of at least 500 and an adhesion promoter and wherein upon mixing of the first part and the second part, curing is achieved with a peak exotherm of less than about 50° C. (120° F.).

26. A composition according to claim 25, wherein the curing agent is a benzoyl peroxide and the curing agent synergist is N,N-dimethyl-p-toluidine.

27. A method for forming a flexible bioadhesive on a tissue, comprising:
contacting the tissue with a composition comprising a compound having an unsaturation index of at least about 500, a curing agent and an adhesion promoter, wherein the composition is curable and has a peak exotherm of less than about 50° C. (120° F.), and
curing the composition to form the flexible bioadhesive on the tissue.

28. A method according to claim 27, wherein the tissue is selected from the group consisting of skin, mucosa, internal organs, bone, tendon, cartilage, enamel, dentin, and fingernails.

29. A flexible bioadhesive on a tissue surface prepared by the method of claim 27.

30. A composition comprising a methacrylated polyetherurethane oligomer, capric/caprylic triglyceride, polycarbophil, camphorquinone, and ethyl-4-dimenthylaminobenzoate.

31. A composition according to claim 30, further comprising fumed silica.

32. A composition according to claim 30, further comprising zinc oxide.

33. A composition according to claim 30, wherein the composition comprises a methacrylated polyetherurethane oligomer in an amount from about 25 percent to about 98 percent by weight based on the total weight of the composition, capric/caprylic triglyceride in an amount from about 2 percent to about 50 percent by weight based on the total weight of the composition, polycarbophil in an amount from about 10 percent to about 50 percent by weight based on the total weight of the composition, camphorquinone in an amount from about 0.05 percent to about 0.30 percent by weight based on the total weight of the composition, and ethyl-4-dimethylaminobenzoate in an amount from about 0.1 percent to about 1.0 percent by weight based on the total weight of the composition.

34. A composition comprising a compound having less than about 40% monomers, an unsaturation index of at least about 500, a curing agent and an adhesion promoter, wherein the composition is curable and has a peak exotherm of less than about 50° C. (120° F.).

35. A method of making a composition comprising the steps of:
selecting a compound having an unsaturation index of at least 500; and
mixing said compound with a curing agent and an adhesion promoter, wherein the mixture is curable and has a peak exotherm of less than about 50° C. (120° F.).

36. The method of claim 35, wherein the curable unsaturated compound comprises less than about 40% monomers.

37. The method of claim 35, wherein the curable unsaturated compound is monomer-free.

* * * * *